United States Patent
Amanullah et al.

(10) Patent No.: US 11,796,438 B2
(45) Date of Patent: Oct. 24, 2023

(54) VUGULAR LOSS SIMULATING VUG TESTER FOR SCREENING AND EVALUATION OF LCM PRODUCTS

(71) Applicant: Saudi Arabian Oil Company, Dhahran (SA)

(72) Inventors: Md Amanullah, Dhahran (SA); Mohammed K. Arfaj, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 17/547,582

(22) Filed: Dec. 10, 2021

(65) Prior Publication Data

US 2022/0099544 A1    Mar. 31, 2022

Related U.S. Application Data

(62) Division of application No. 16/152,219, filed on Oct. 4, 2018, now abandoned.

(51) Int. Cl.
*G01N 11/02*    (2006.01)

(52) U.S. Cl.
CPC .................................. *G01N 11/02* (2013.01)

(58) Field of Classification Search
CPC ...................................................... G01N 11/04
See application file for complete search history.

(56) References Cited

U.S. PATENT DOCUMENTS

| | | |
|---|---|---|
| 2,646,678 A | 7/1953 | Standing |
| 2,733,595 A | 2/1956 | Twining |
| 4,781,525 A | 11/1988 | Hubbard |
| 5,037,454 A | 8/1991 | Mann |

(Continued)

FOREIGN PATENT DOCUMENTS

| | | |
|---|---|---|
| CN | 2575293 | 9/2003 |
| CN | 102337859 | 2/2012 |

(Continued)

OTHER PUBLICATIONS

AU Examination Report in Australian Appln. No. 2018236217, dated May 26, 2022, 4 pages.
Gulf Cooperation Council Examination Report issued in GCC Application No. GC 2018-34953 on Oct. 8, 2019, 4 pages.
GCC Examination Report in Gulf Cooperation Council Appln. No. GC 2018-34953, dated Jan. 27, 2021, 3 pages.
GCC Examination Report in Gulf Cooperation Council Appln. No. GC 2019-38407, dated Oct. 30, 2020, 5 pages.
International Search Report and Written Opinion issued in International Application No. PCT/US2018/022229 dated Jul. 6, 2018, 15 pages.

(Continued)

*Primary Examiner* — Jamel E Williams
*Assistant Examiner* — Alex T Devito
(74) *Attorney, Agent, or Firm* — Fish & Richardson P.C.

(57) ABSTRACT

An apparatus to simulate fluid loss through vugs in formations includes a housing defining an inner volume, and having a first end and a second end. The inner volume represents an inner region of a wellbore formed in a formation containing a vugular loss zone. The housing can receive wellbore fluid within the inner volume. A first cover late, which sealingly covers the first end, represents a first volumetric boundary of the inner region of the wellbore. A second cover plate, which sealingly covers the second end, represents a second volumetric boundary of the inner region of the wellbore. An outlet in the second cover plate can be switched between open and closed states. The outlet in the open state represents a vug in the inner wall of the wellbore. The apparatus includes a pressure port configured to transmit fluidic pressure in a direction of gravity within the inner volume and to apply the fluidic pressure to the wellbore fluid within the inner volume.

6 Claims, 9 Drawing Sheets

(56) References Cited

U.S. PATENT DOCUMENTS

| | | | |
|---|---|---|---|
| 5,161,407 | A | 11/1992 | Ankeny et al. |
| 6,055,850 | A | 5/2000 | Turner et al. |
| 7,900,504 | B2 | 3/2011 | Huynh |
| 8,151,633 | B2 | 4/2012 | Jamison et al. |
| 8,863,567 | B2 | 10/2014 | Jappy et al. |
| 8,972,235 | B2 | 3/2015 | Murphy et al. |
| 9,285,355 | B2 | 3/2016 | Murphy et al. |
| 9,388,333 | B2 | 7/2016 | Savari |
| 9,587,490 | B2 | 3/2017 | Kaarigstad et al. |
| 9,714,565 | B2 | 7/2017 | Blue et al. |
| 10,041,871 | B2 | 8/2018 | Jamison et al. |
| 10,180,063 | B2 | 1/2019 | Murphy et al. |
| 10,584,582 | B2 | 3/2020 | Murphy et al. |
| 11,111,742 | B2 | 9/2021 | Amanullah et al. |
| 2008/0236891 | A1 | 10/2008 | Huynh |
| 2010/0032031 | A1 | 2/2010 | Neal |
| 2010/0139387 | A1 | 6/2010 | Jamison et al. |
| 2011/0120217 | A1 | 5/2011 | Huynh et al. |
| 2011/0290012 | A1 | 12/2011 | Jappy et al. |
| 2012/0152000 | A1 | 6/2012 | Jamison |
| 2013/0192358 | A1 | 8/2013 | Murphy et al. |
| 2013/0218545 | A1 | 8/2013 | Murphy |
| 2013/0298662 | A1 | 11/2013 | Jamison et al. |
| 2014/0102188 | A1 | 4/2014 | Murphy et al. |
| 2014/0182369 | A1 | 7/2014 | Blue et al. |
| 2014/0216149 | A1 | 8/2014 | Zhou et al. |
| 2015/0059447 | A1 | 3/2015 | Rickards et al. |
| 2016/0033382 | A1 | 2/2016 | Jamison et al. |
| 2016/0061701 | A1 | 3/2016 | Amanullah et al. |
| 2016/0130939 | A1 | 5/2016 | Murphy et al. |
| 2018/0266197 | A1 | 9/2018 | Amanullah et al. |
| 2019/0112922 | A1 | 4/2019 | Murphy et al. |
| 2020/0110014 | A1 | 4/2020 | Amanullah et al. |
| 2020/0110015 | A1 | 4/2020 | Amanullah et al. |
| 2020/0370431 | A1 | 11/2020 | Amanullah et al. |

FOREIGN PATENT DOCUMENTS

| | | |
|---|---|---|
| CN | 202690036 | 1/2013 |
| CN | 103270240 | 8/2013 |
| CN | 103510944 | 1/2014 |
| CN | 103953332 | 7/2014 |
| CN | 107101896 | 8/2017 |
| JP | S 58109582 A | 6/1983 |
| JP | S 6259690 A | 3/1987 |
| JP | 2008034848 A | 2/2008 |
| KR | 101734988 | 5/2017 |
| WO | WO 9413954 | 6/1994 |
| WO | WO 2009029451 | 3/2009 |
| WO | WO 2010064009 | 6/2010 |
| WO | WO 2013126287 | 8/2013 |
| WO | WO 2018005575 | 1/2018 |
| WO | WO 2018169992 | 9/2018 |

OTHER PUBLICATIONS

International Search Report and Written Opinion issued in International Application No. PCT/US2019/054408 dated Feb. 21, 2020, 18 pages.

CN Office Action in Chinese Appln. No. 201880018602.6, dated Sep. 15, 2021, with English Translation, 28 pages.

JP Office Action in Japanese Appln. No. 2019-551369, dated Feb. 7, 2022, with English Translation, 10 pages.

EP Office Action Pursuant to Article 94(3) EPC in European Appln. No. 18715350.7-1001, dated Feb. 23, 2022, 4 pages.

Fann, "Permeability Plugging Apparatus (PPA)," XP055060626, Fann product information, Drilling Fluids, Jan. 1, 2007, 2 pages.

Hettema et al., "Development of an Innovative High-Pressure Testing Device for the Evaluation of Drilling Fluid Systems and Drilling Fluid Additives Within Fractured Permeable Zone," Retrieved from the Internet: URL: <https://www.onepetro.org/download/conference-paper/OMC-2007-082? i d=conference-paper/OMC-2007-082>, Offshore Mediterranean Conference and Exhibition, Mar. 28-30, 2007, 14 pages.

Miller et al., "Laboratory apparatus improves simulation of lost circulation conditions," AADE-13-FTCE-09, AADE, American Association of Drilling Engineers, presented at the 2013 AADE National Technical Conference and Exhibition, Feb. 26-27, 2013, 8 pages.

Smith and Growcock, "AADE-11-DF-HO-24 Wellbore Strengthening While Drilling Above and Below Salt in the Gulf of Mexico," presented at the 2008 AADE Fluids Conference and Exhibition on Apr. 8-9, 2008, 6 pages.

Wei, "Application and Practice of Drilling Matching Technology in Northeast Sichuan," Geological Publishing House, Nov. 2007, 115-116, English Abstract only.

Whitfill and Miller, "AADE-08-NTCE-21 Developing and Testing Lost Circulation Materials," presented at the 2008 AADE Fluids Conference and Exhibition on Apr. 8-9, 2008, 11 pages.

VUGULAR LOSS SIMULATING VUG TESTER FOR SCREENING AND EVALUATION OF LCM PRODUCTS

CROSS-REFERENCE TO RELATED PATENT APPLICATIONS

This application is a divisional of and claims the benefit of priority to U.S. patent application Ser. No. 16/152,219, filed Oct. 4, 2018, the contents of which are incorporated by reference herein.

TECHNICAL FIELD

This specification relates to laboratory equipment to simulate flow through hydrocarbon-carrying formations and through wellbores drilled in such formations.

BACKGROUND

Hydrocarbons entrapped in formations can be recovered by forming wellbores in the formations and producing the hydrocarbons through the wellbores. Forming a wellbore through a formation involves drilling into the formation from a surface of the formation to a desired depth. For example, a drill bit attached to an end of a drill string can be rotated to drill through the formation, thereby forming the wellbore. During drilling, a drilling fluid can be circulated from the surface through the drill string and ports formed in the drill bit. The drilling fluid can return to the surface through an annulus formed between the drill string and an inner wall of the wellbore. The drilling fluid serves several functions including, for example, cooling the drill bit, carrying debris (called cuttings) out of the wellbore, providing weight on bit, among others.

In some portions of the formation, the rocks can have cavities (for example, voids or pores) called vugs. In some instances, the drilling fluid flowing through the annulus to the surface can flow into the formation through the vugs and be lost. Such portions of the formation into which the drilling fluid is lost are called vugular loss zones.

SUMMARY

This specification describes technologies relating to simulating fluid loss through vugs in hydrocarbon-carrying formations.

Certain aspects of the subject matter described here can be implemented as a laboratory test apparatus. The apparatus includes a housing defining an inner volume. The housing includes a first end and a second end. The inner volume represents an inner region of a wellbore at least partially formed in a formation containing a vugular loss zone of the wellbore. The housing is configured to receive wellbore fluid within the inner volume. The apparatus includes a first cover late configured to sealingly cover the first end. The first cover plate represents a first volumetric boundary of the inner region of the wellbore. The apparatus includes a second cover plate configured to sealingly cover the second end. The second cover plate represents a second volumetric boundary of the inner region of the wellbore. The second cover plate defines an outlet configured to be switched between an open state and a closed state. The outlet in the open state represents a vug in the inner wall of the wellbore. The apparatus includes a pressure port configured to transmit fluidic pressure in a direction of gravity within the inner volume and to apply the fluidic pressure to the wellbore fluid within the inner volume.

Aspects of the disclosure taken alone or combinable with any of the other aspects can include the following features. In the open state, the outlet is configured to prevent flow of the wellbore fluid in response to the fluidic pressure. In the closed state, the outlet is configured to permit flow of the wellbore fluid in response to the fluidic pressure.

Aspects of the disclosure taken alone or combinable with any of the other aspects can include the following features. A dimension of the outlet is at least 10 millimeters.

Aspects of the disclosure taken alone or combinable with any of the other aspects can include the following features. The apparatus includes a wired screen defining an opening. The wired screen is positioned at the second end aligning the outlet and the opening. The wired screen cooperates with the second cover plate to sealingly cover the second end.

Aspects of the disclosure taken alone or combinable with any of the other aspects can include the following features. The housing is transparent.

Aspects of the disclosure taken alone or combinable with any of the other aspects can include the following features. The apparatus includes a flexible hose coupled to the outlet. The flexible hose represents a flow pathway through the vug within the vugular loss zone starting at the inner wall of the wellbore.

Aspects of the disclosure taken alone or combinable with any of the other aspects can include the following features. The first end is an upper end and the second end is a lower end vertically below the first end. The first cover plate defines an opening configured to fluidically mate with the pressure port.

Aspects of the disclosure taken alone or combinable with any of the other aspects can include the following features. The apparatus includes a pressure inlet pipe coupled to the pressure port. The pressure inlet pipe is configured to transmit the fluidic pressure from a pressure source into the housing through the pressure port.

Aspects of the disclosure taken alone or combinable with any of the other aspects can include the following features. The apparatus includes a mounting stand attached to the first end of the housing. The mounting stand is configured to maintain the housing in a substantially vertical orientation.

Certain aspects of the subject matter described here can be implemented as a laboratory test apparatus. The apparatus includes a mounting stand. The apparatus includes a housing including an upper end attached to the mounting stand. The housing extends downward from the mounting stand and terminates at a lower end below the mounting stand. The housing defines an inner volume representing an annulus formed by an inner wall of a wellbore being drilled in a hydrocarbon-carrying formation and an outer wall of a drill string used to drill the wellbore. The housing includes wellbore fluid filling the inner volume. The apparatus includes a lower cover plate configured to sealingly cover the lower end. The lower cover plate represents the inner wall of the wellbore and defines an outlet configured to be switched between an open state and a closed state. The outlet in the open state represents a vug in the inner wall of the wellbore. The apparatus includes a pressure port defined near the upper end of the housing. The pressure port is configured to transmit fluidic pressure in a downward direction from the upper end towards the lower end through the wellbore fluid and to apply the fluidic pressure to the wellbore fluid within the inner volume.

Aspects of the disclosure taken alone or combinable with any of the other aspects can include the following features. The apparatus includes a wired screen defining a second opening. The wired screen is positioned at the second end aligning the first opening and the second opening. The wired screen cooperates with the second cover plate to sealingly cover the lower end.

Aspects of the disclosure taken alone or combinable with any of the other aspects can include the following features. The apparatus includes an upper cover plate configured to sealingly cover the upper end.

Aspects of the disclosure taken alone or combinable with any of the other aspects can include the following features. The pressure port is formed through a circumferential wall of the housing adjacent the upper cover plate.

Aspects of the disclosure taken alone or combinable with any of the other aspects can include the following features. The pressure port is formed in the upper cover plate adjacent the housing.

Aspects of the disclosure taken alone or combinable with any of the other aspects can include the following features. The housing is transparent.

Certain aspects of the subject matter described here can be implemented as a method of simulating loss of wellbore fluid in a vugular loss zone. A housing defining an inner volume is filled with wellbore fluid. The inner volume represents an inner region of a wellbore at least partially formed in a loss-triggering subsurface formation. A first end and a second end of the housing are sealed with a first cover plate and a second cover plate, respectively. The second cover plate includes an outlet switchable between an open state and a closed state. The outlet in the open state represents a vug in the inner wall of the wellbore. With the outlet in the closed state, fluidic pressure is applied in a direction of gravity from the first end of the housing toward the second end. Sealing an blocking properties of the wellbore fluid to flow through the vug in the inner wall of the wellbore are evaluated based on a comparison of results of applying the fluidic pressure in the closed state and applying the fluidic pressure in the open state.

Aspects of the disclosure taken alone or combinable with any of the other aspects can include the following features. The wellbore fluid with which the interior volume is filled is a first wellbore fluid. To evaluate the properties of the wellbore fluid, an additive is mixed to a second wellbore fluid having a volume equal to that of the first wellbore fluid. The additive is configured to alter the properties of the wellbore fluid. The housing is filled with a mixture of the second wellbore fluid and the additive. The first end and the second end of the housing are sealed with the first cover plate and the second cover plate. With the outlet in the closed state, the fluidic pressure in the direction of gravity is applied from the first end of the housing toward the second end. With the outlet in the open state, the fluidic pressure in the direction of gravity is applied from the first end of the housing toward the second end. The sealing and blocking properties of the wellbore fluid to flow through the vug in the inner wall of the wellbore are evaluated based on a comparison of results of flow of the first wellbore fluid and the second wellbore fluid through the outlet in the open state.

Aspects of the disclosure taken alone or combinable with any of the other aspects can include the following features. The housing is transparent. The properties of the wellbore fluid can be visually evaluated based on visual inspection of an effect of applying the fluidic pressures on the wellbore fluid in the inner volume with the outlet in the closed state an with the outlet in the open state.

Aspects of the disclosure taken alone or combinable with any of the other aspects can include the following features. A flexible hose can be coupled to the outlet. The flexible hose represents a flow pathway through the vug within a formation starting at the inner wall of the wellbore. Flow through the flow pathway can be visually observed with the outlet in the open state.

The details of one or more implementations of the subject matter described in this specification are set forth in the accompanying drawings and the description that follows. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
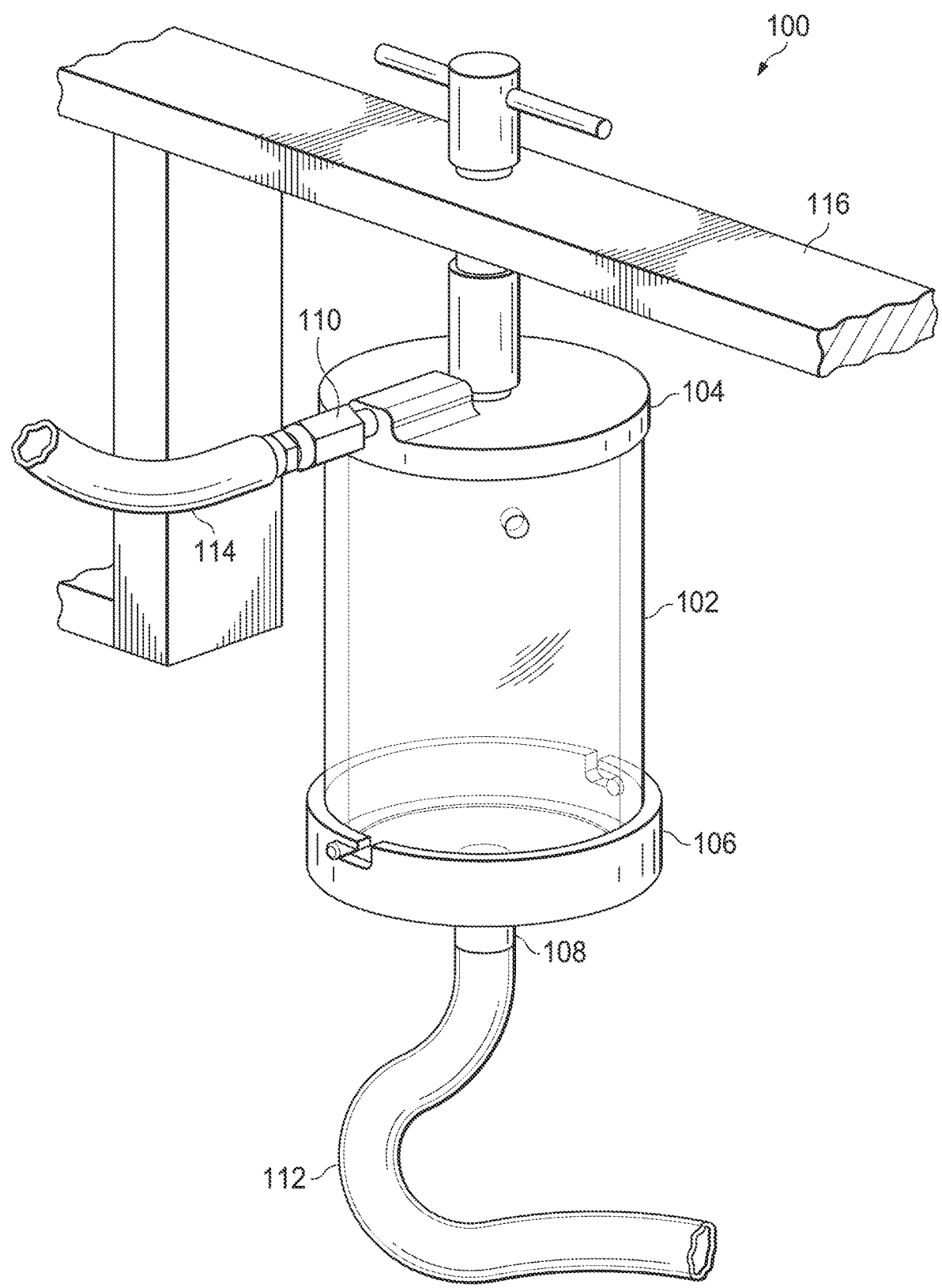
FIG. 1 is a schematic diagram of a laboratory test apparatus for simulating flow through vugular loss zones.

Wellbores can be formed in hydrocarbon-carrying formations to produce hydrocarbons (for example, oil, gas, combinations of them or similar hydrocarbons) entrapped in the formations. The formations can include one or more zones, for example, rubble loss zone, high permeability loss zone, super permeability loss zone, mildly fractured loss zone, cavernous loss zone, vugular loss zone, highly fractured loss zone, faulted loss zone (to name a few), each of which represents a portion of the formation through why wellbore fluids can be lost. Vugular loss refers to the loss of wellbore fluids flowed through vugs, that is, cavities or pores, in rocks in the hydrocarbon-carrying formations. Vugular loss can occur, for example, when drilling a wellbore in a formation. As the drilling fluid flows past a portion of the hydrocarbon-carrying formation that includes rocks with vugs, a portion of the drilling fluid may flow into the vugs and be lost. In another example, vugular loss can occur when produced fluids, such as hydrocarbons, flow towards a surface of the wellbore. As the produced fluids flow towards the surface, the fluids near the inner wall of the wellbore may flow into the vugs and be lost. Vugs in a vugular loss zone can have sizes ranging from a few millimeters to tens of centimeters. The vug may expand in size within the rock. The vugs can be isolated, or moderately or highly interconnected. Subsurface formations with interconnected vugs can cause significant loss in wellbore fluids.

This disclosure describes a laboratory test apparatus to simulate vugular loss of wellbore fluids, for example, drilling fluid, hydraulic fracturing fluid, loss circulation material, or any fluid flowed through a vugular loss zone of a hydrocarbon-carrying formation or used in wellbore operations. Implementations of the laboratory test apparatus described in this disclosure can simulate flow of wellbore fluids past rocks with vugs in the hydrocarbon-carrying formation. The apparatus described here can be implemented as a fit-for-purpose test apparatus that can simulate vugular morphologies including vugular depths of subsurface loss zones for realistic simulation of wellbore fluid loss events. The apparatus described here can simulate overbalance pressures of at least 100 pounds per square inch (psi) without leakage. The overbalance pressures can be associated with the equivalent circulating density (ECD) effect while drilling and the surge effect while making a tripping operation. The apparatus can be implemented to screen and evaluate wellbore fluids, for example, loss circulation materials (LCMs) products, slurries and pills to identify fluids that can mitigate, minimize or prevent loss through vugular loss zones. The apparatus can also be implemented to simulate flow through vugular flow pathways. By evaluating wellbore fluids using the apparatus described here, the success rate of wellbore treatments (for example, LCM treatments can be improved). Due to see-through nature, it also allows to make visual observation of the sealing and plugging mechanism and allows accurate analyses of image data.

Figure 2:
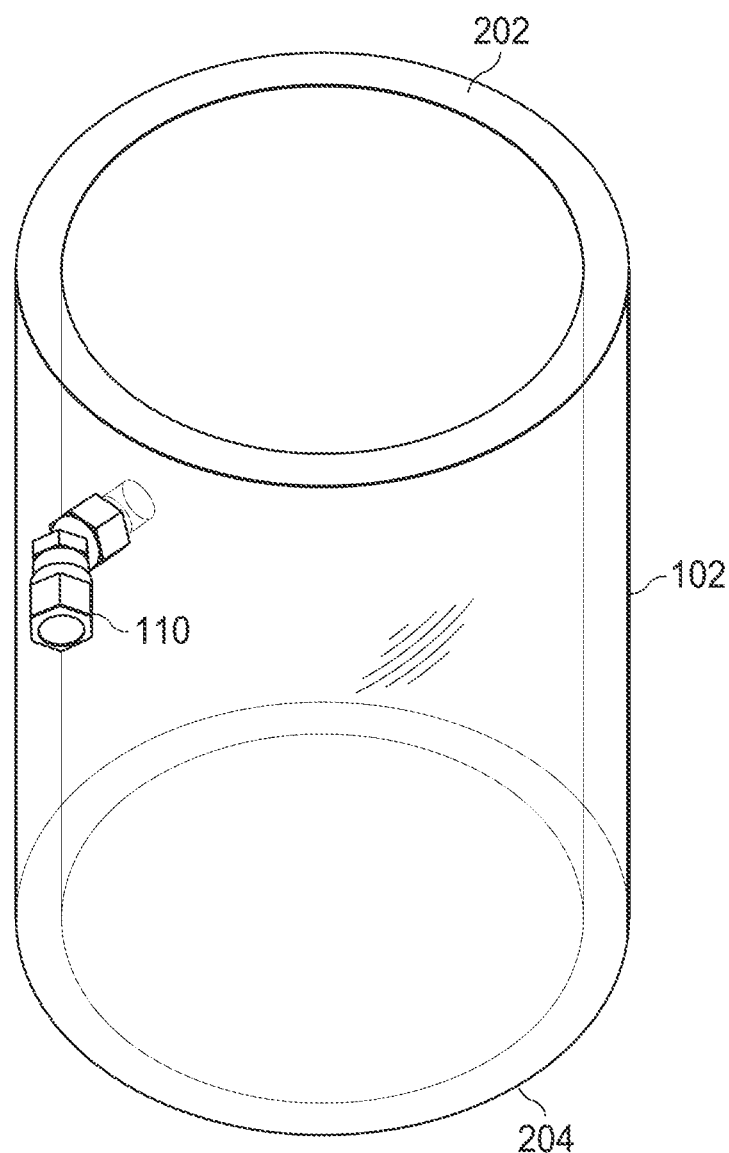
FIG. 2 is a schematic diagram of a housing of the apparatus of FIG. 1.

FIG. 1 is a schematic diagram of a laboratory test apparatus 100 for simulating flow through vugular loss zones. The apparatus 100 includes a housing 102 defining an inner volume. FIG. 2 is a schematic diagram of the housing 102. In some implementations, the housing 100 can be a cylindrical pipe with a circular cross-section. Cross-sections of other polygonal shapes are also possible. The housing 102 can be made of a transparent material (for example, polymethyl methacrylate) or metal. The housing 100 includes a first end 202 and a second end 204. For example, when the housing 100 is vertically oriented with a longitudinal axis of the housing being substantially perpendicular to a horizontal surface, the first end 202 is the upper end and the second end 204 is the lower end. By "substantially perpendicular," it is meant that an orientation of the housing 100 can deviate from an absolute perpendicular (that is, from a 90 degree orientation) by a few degrees (such as, 5 degrees). The inner volume defined by the housing 102 between the first end 202 and the second end 204 represents an inner region of a wellbore at least partially formed in a hydrocarbon-carrying formation. The housing 102 can receive wellbore fluid within the inner volume.

The apparatus 100 includes a cover plate 104 that can sealingly cover the first end 202. The cover plate 104 can have a cross-section that matches that of the housing 102. In general, the cover plate 104 can be secured onto the first end 202 to avoid fluid leakage from the first end 202 when a pressure within the housing 102 is increased. In some implementations, the cover plate 104 can be press fit around the first end 202. In some implementations, the cover plate 104 can be screwed on to the first end 202 with or without a sealing element, for example, O-ring or similar sealing element. For example, the choice of materials with which the housing 102 and the cover plate 104 are manufactured and the mechanism by which the housing 102 and the cover plate 104 are attached can withstand pressures as high as and including 100 pounds per square inch (psi) without fluid leakage. In one example, the housing 102 can be about 10 inches long, have an outer diameter of about 3.5 inches and an inner diameter of about 3.25 inches with a wall thickness of about 0.25 inches. In the context of dimensions, the term "about" means that a dimension can vary from a specified value by a range that depends on the tolerances of the machines using which a component having the dimension is constructed.

The apparatus 100 includes a cover plate 106 that can sealingly cover the second end 204. The cover plate 106 can have a cross-section that matches that of the housing 102. In general, the cover plate 106 can be secured onto the second end 204 to avoid fluid leakage from the second end 204 when a pressure within the housing 102 is increased. In some implementations, the cover plate 106 can be press fit around the second end 204. In some implementations, the cover plate 106 can be screwed on to the second end 204 with or without a sealing element, for example, O-ring or similar sealing element. For example, the choice of materials with which the housing 102 and the cover plate 106 are manufactured and the mechanism by which the housing 102 and the cover plate 106 are attached can withstand pressures as high as and including 100 pounds per square inch (psi) without fluid leakage.

Figure 3A:
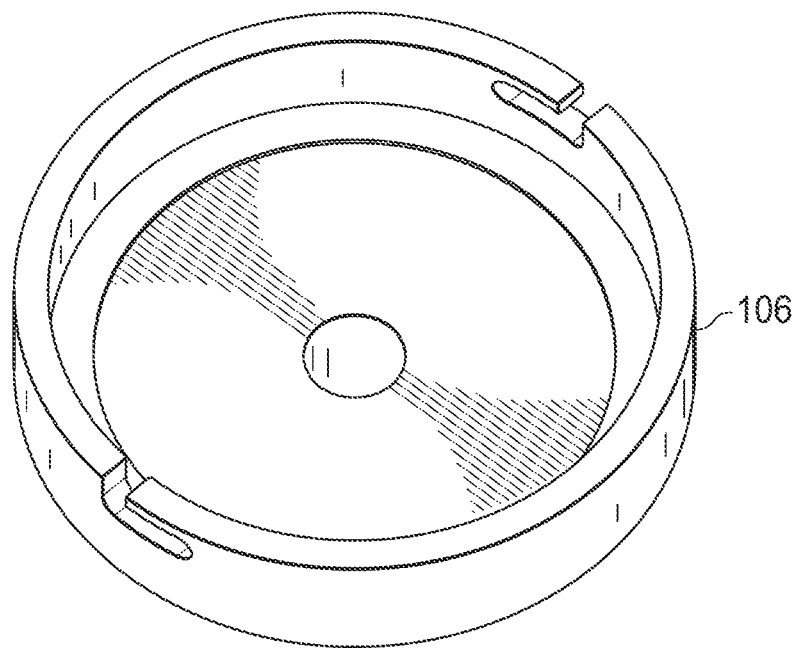
FIGS. 3A and 3B are schematic diagrams of an inner view and an outer view, respectively, of a cover plate of the apparatus of FIG. 1.
Figure 3B:
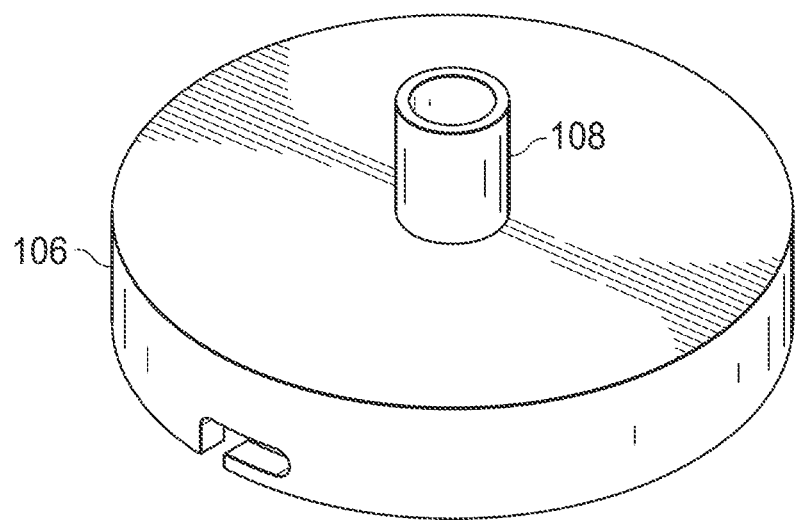

FIGS. 3A and 3B are schematic diagrams of an inner view and an outer view, respectively, of the cover plate 106. The inner view shows the sealing rubber gasket to create a tight seal to prevent any leak of fluid and air pressure and the central exit hole that is communicably connected to the test cell when mounted together. The second cover plate 106 defines an outlet 108 that can be switched between an open state and a closed state. For example, a removable blunt clip can be used to switch the second cover plate 106 between the open and closed states. In some implementations, the outlet 108 can be circular and have a diameter of substantially 10 millimeters (mm). By "substantially 10 mm," it is meant that the diameter of the outlet 108 can vary from 10 mm by a range based on tolerances of tools used to make the outlet 108. The diameter of the outlet 108 can be chosen based on the size of the vug in the rock past which the wellbore fluid flows in a real wellbore. Thus, in some implementations, a second cover plate with an outlet that ranges between substantially 5 mm and substantially 20 mm can be used. In some implementations, the outlet 108 can be non-circular (for example, polygonal or non-geometric in shape) with an effective diameter equal to the diameter of the circular outlet 108. In some implementations, the outlet 108 can be an opening formed in the second cover plate 106.

Figure 5:
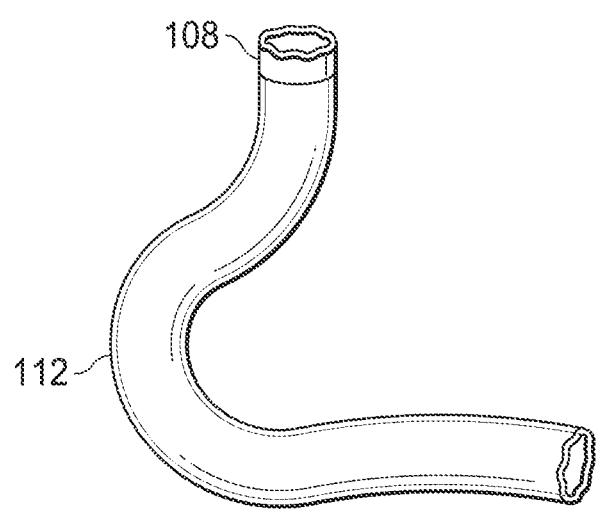
FIG. 5 is a schematic diagram of a flexible hose of the apparatus of FIG. 1.
Figure 6A:
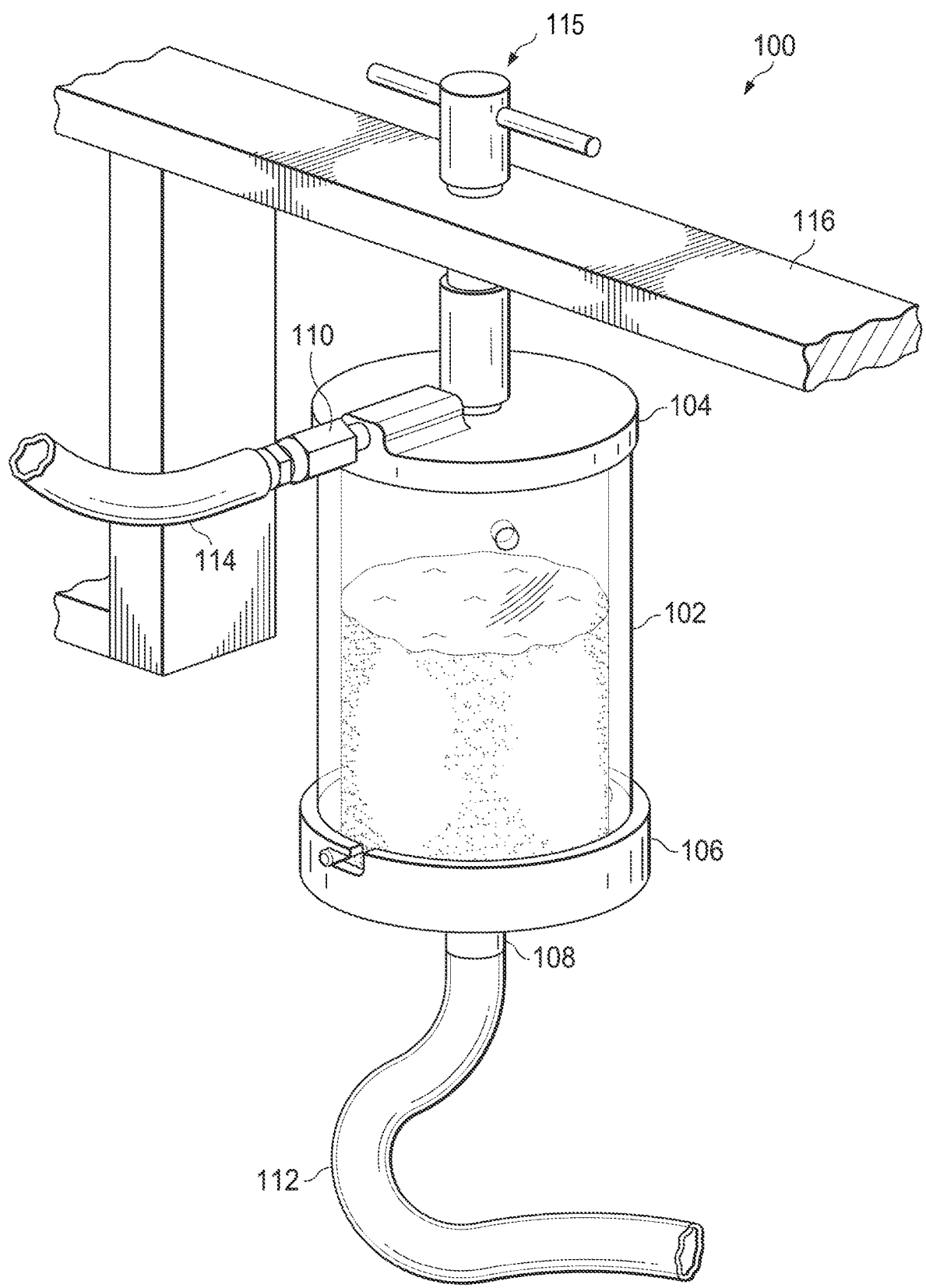
FIGS. 6A and 6B are schematic diagrams of a first flow simulation test performed using the apparatus of FIG. 1.
Figure 6B:
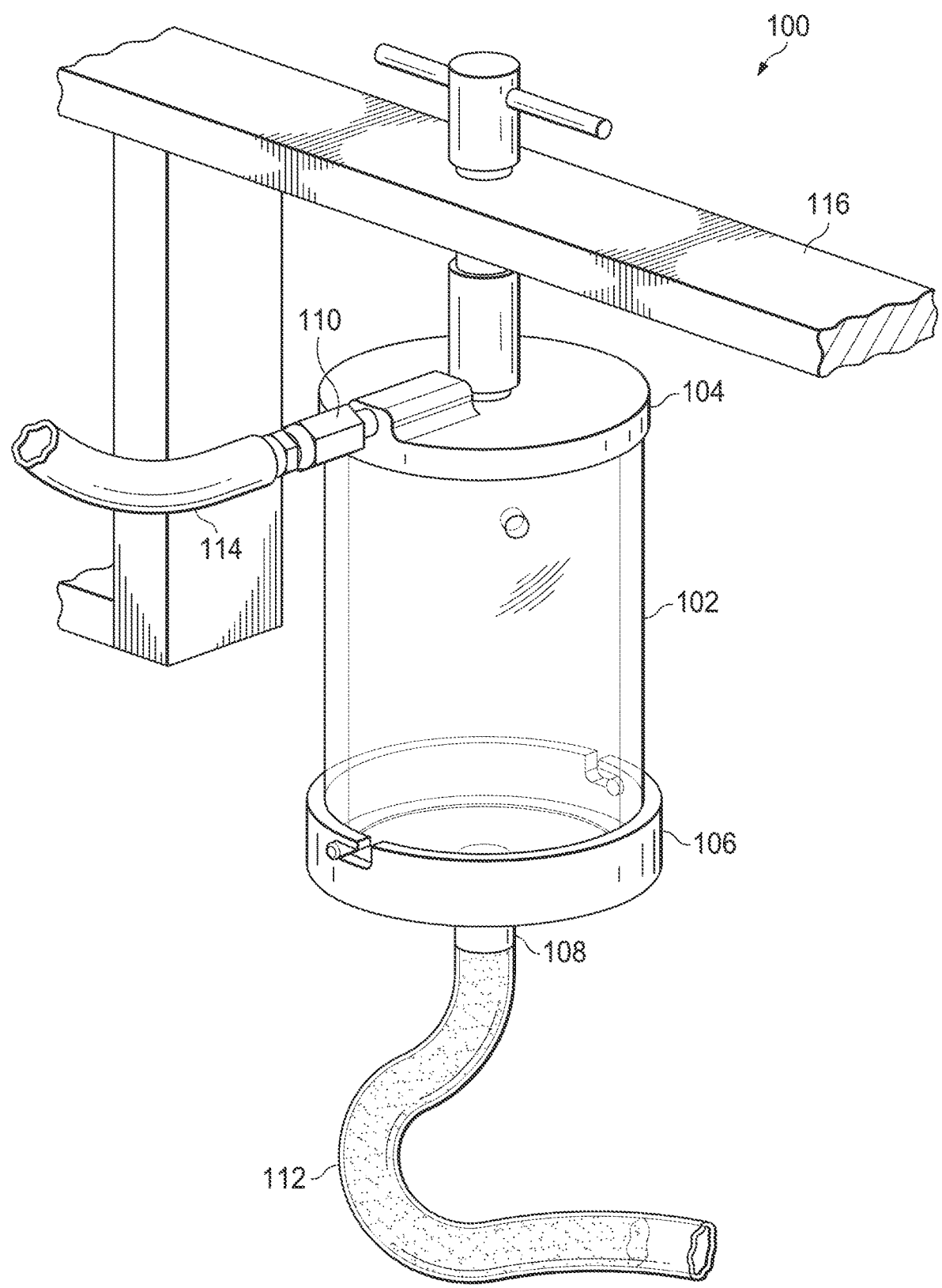
Figure 6C:
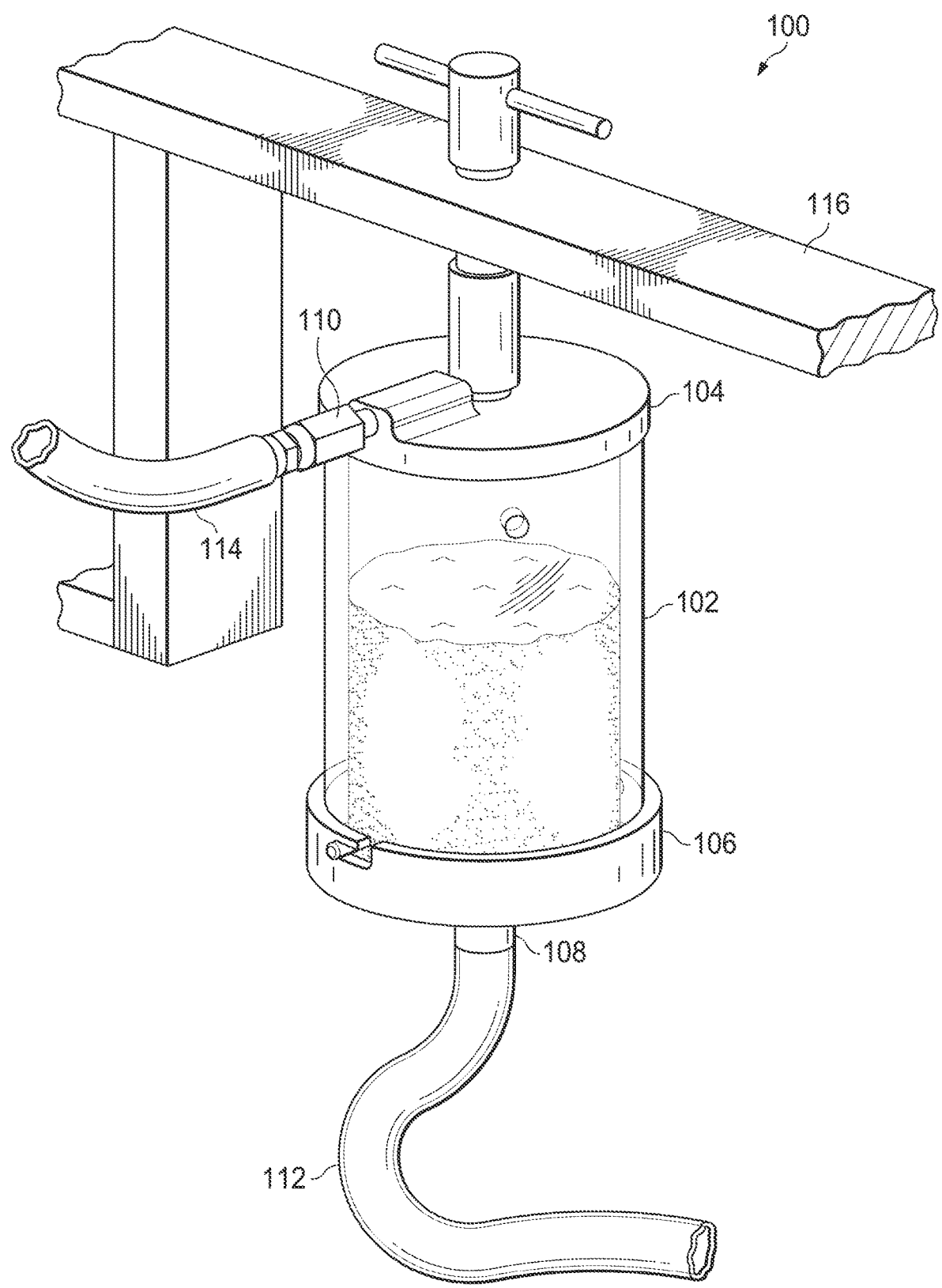
FIGS. 6C and 6D are schematic diagrams of a second flow simulation test performed using the apparatus of FIG. 1.
Figure 6D:
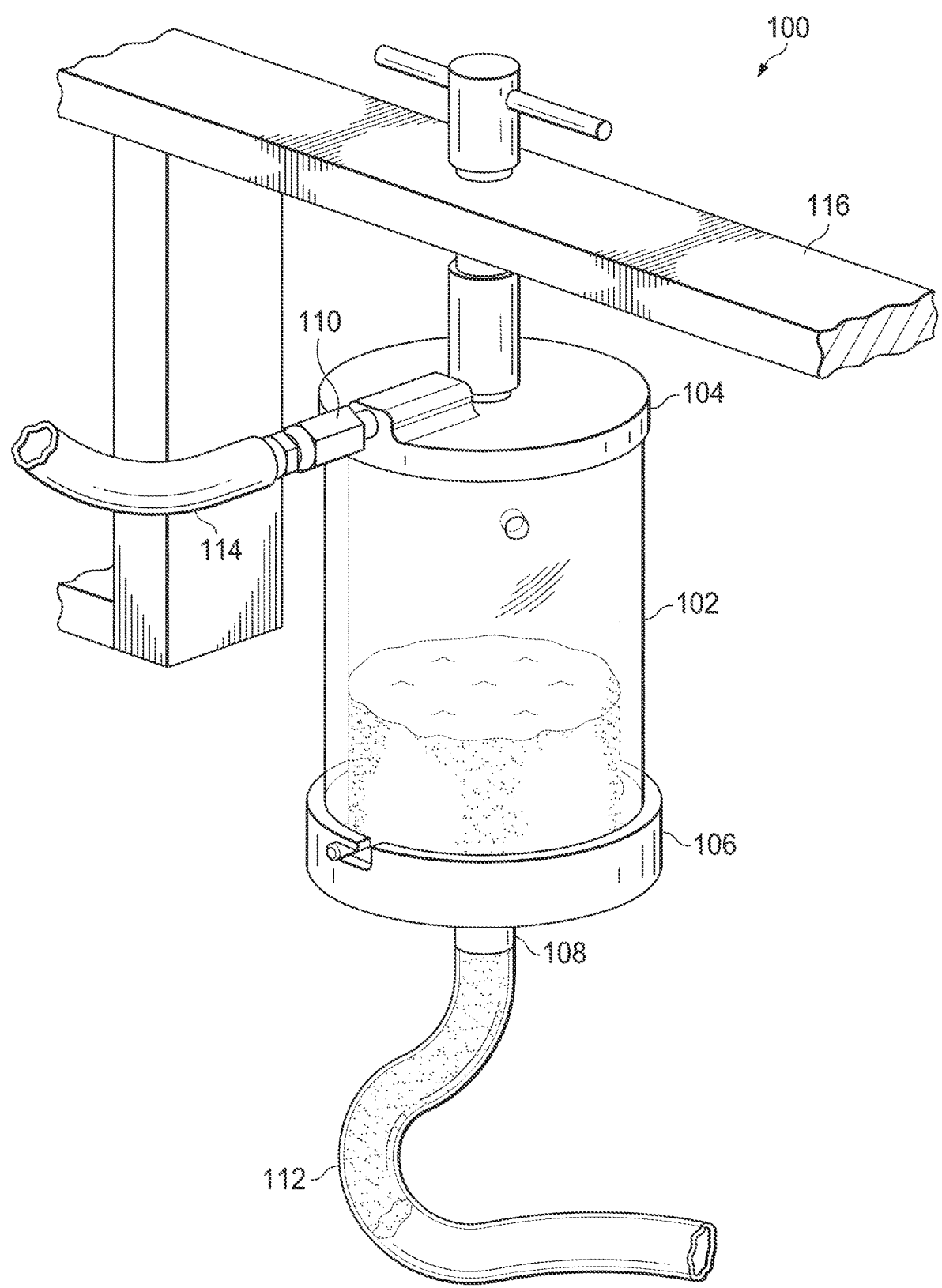

In some implementations, as shown in FIG. 3B, the outlet 108 can additionally include a pipe with an inner diameter equal to a size of the opening and a length extending from the outer surface of the second cover plate 106. FIG. 5 is a schematic diagram of a flexible hose 112 that can coupled to the outlet 108. The hose 112 can have a length selected to represent a vugular flow pathway, that is, an extended pathway of a vug through a rock in the hydrocarbon-carrying formation. The wellbore fluid can enter the rock through the vug and be carried through the vugular flow pathway. For example, the flexible hose 112 can have a length of substantially 3 feet. By "substantially 3 feet," it is meant that a length of the hose 112 can vary from 3 feet by a few inches (such as, by 6 inches). The flexibility of the hose 112 permits twisting or turning the hose 112 different orientations to simulate the tortuosity of the vugular flow pathway in a real rock. In some implementations, a hose of different length (longer or shorter) can be chosen. In some implementations, the apparatus 100 can be implemented without a hose. In some implementations, the flexible hose 112 can be transparent. Using a transparent housing 102 or a transparent flexible hose 112 or both can allow visual evaluation of the properties of fluid flow, for example, imaging flow (or lack of flow) through the housing 102 or the flexible hose 112, for example, using imaging equipment (such as, cameras, video cameras or other imaging equipment) and evaluating the captured images, for example, either manually or automatically (that is, using a computer system) or both to further study the flow properties of the fluids in the housing 102 or the flexible hose 112 or both.

The apparatus 102 includes a pressure port 110 configured to transmit fluidic pressure (for example, pressure of a flowing gas such as air, nitrogen or similar gas) in a direction of gravity within the inner volume and to apply the fluidic pressure to the wellbore fluid within the inner volume. In some implementations, the pressure port 110 is formed in the cover plate 104 that sealingly covers the first end 202 (FIG. 1). In some implementations, the pressure port 110 is formed on a side of the housing 102 that is near the first end 202 (FIG. 2). The pressure port 110 can be coupled to a pressure inlet pipe 118, which can transmit the fluidic pressure from a pressure source (not shown) into the housing 102 through the pressure port 110. The top lid 104 already has a built in pressure port 110 to allow the entry of pressurized gas. A high pressure rubber hose 114 is connected to the built-in port to transmit air pressure from a gas cylinder connected to it. When the outlet 108 is in the closed state, fluidic pressure applied within the housing 102 through the pressure port 110 is sealingly retained within the housing 102 by the cover plates 104 and 106. When the outlet 108 is in the open state, the fluidic pressure can escape through the outlet 108. The wellbore fluid that at least partially fills the housing can affect a quantity of the fluidic pressure that can escape. For example, the properties of certain wellbore fluid can prevent any of the fluidic pressure from escaping through the outlet 108. Properties of other wellbore fluids can cause the wellbore fluids to flow out of the housing 102 through the outlet 108 responsive to the fluidic pressure.

In some implementations, the apparatus 100 includes a mounting stand 116 to which the housing 102 is attached. For example, the upper end (that is, the first end 104) of the housing 102 is attached to the mounting stand 116 such that the housing 102 extends vertically below the mounting stand 116. In some implementations, the mounting stand 116 can maintain the housing 102 in a substantially vertical orientation. For example, the mounting stand 116 can be a horizontal member (such a horizontal piece of wood or other material) that defines a coupling section 115 to which the first end 104 of the housing 102 is coupled.

Figure 4:
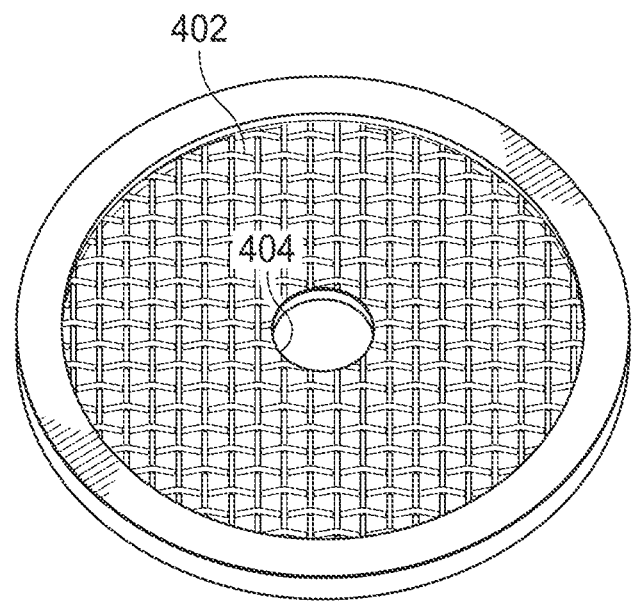
FIG. 4 is a schematic diagram of a wired screen of the apparatus of FIG. 1.

FIG. 4 is a schematic diagram of a wired screen 402 that can be included in the apparatus 100. The wired screen 402 can be a mesh that permits particles smaller than a certain size to flow through but retains particles larger than the size. The wired screen 402 defines an opening 404. The size and shape of the opening 404 can be less or the same as that of the outlet 108. The mesh size can be as small as or smaller than 250 micron mesh. The mesh size can be larger than 250 micron mesh but less than that of the outlet 108. The wired screen 402 can be positioned at the second end 106 aligning the outlet 108 and the opening 404. The wired screen 402 cooperates with the second cover 204 to sealingly cover the second end 104. The screen creates a tight seal by virtue of the softer nature of the peripheral solid part of the screen. The housing 102 sits on the solid part to make a tight seal to prevent any leaking.

The housing 102, the cover plate 104 sealingly covering the first end 202 and the cover plate 106 sealingly covering the second end 204 collectively represent an inner region of a wellbore that is at least partially formed in a loss zone of the wellbore. For example, the inner region can be used to represent a wellbore that is being drilled in the formation. Alternatively, the inner region can be used to represent a wellbore through which fluids (for example, drilling mud) are lost in the loss zone. When the outlet 108 is in the closed state, the inner volume of the housing 102 simulate a wellbore without the presence of a vugular loss zone. However, when the outlet 108 is in the open state, the inner volume of the housing 102 simulates the presence of a vugular loss zone in the near wellbore formation that causes severe loss of drilling mud while drilling. By at least partially or completely filling the inner volume of the housing 102 and applying fluidic pressure to the wellbore fluid, for example, via the pressure port 110, flow of the wellbore fluid past a rock having a vug or past vugular loss zones can be simulated. Measurements made during the simulation, for example, fluidic pressure measurements across the housing 102 or other measurements, can be used to determine the sealing and blocking properties of the wellbore fluid. Knowing the properties of the wellbore fluid under simulated conditions can yield useful knowledge about the behavior of the wellbore fluid when flowing past real vugs or vugular loss zones in a real wellbore.

FIGS. 6A-6D are schematic diagrams of flow simulation tests performed using the apparatus 100.

Example 1

In a first test, a drilling phase of a wellbore drilling system was simulated. The drilling mud used in the test did not include any loss circulation materials. In the test, 65 pounds per cubic feet (pcf) bentonite mud was used. About 500 cubic centimeters (cc) of the mud was placed in the housing 100 with the outlet 108 in a closed state. In the test illustrated by FIG. 6A, a pressure of 100 psi was applied through the pressure port 110 to simulate the drilling operation with 100 psi overbalance pressure without encountering any loss zones. In the test illustrated by FIG. 6B, the outlet 108 was subsequently opened to simulate encountering a vugular loss zone with a vug size of 10 mm. Visual observation of the test result, enabled by the transparent nature of the housing 102, indicated the immediate loss of the entirety of the bentonite mud through the outlet 108. The result indicates that massive loss zones allow rapid escape of whole mud through the vugs in a very short period.

Example 2

In a second test, the drilling phase of the wellbore drilling system was once again simulated, this time by adding LCM to the drilling mud. In the test, 65 pounds per cubic feet (pcf) bentonite mud mixed with 30 parts per billion (ppb) of a LCM (ARC fiber) was used. The LCM is designed for severe loss control and has a variable fiber length ranging from 4.77 mm up to a size that can pass through mesh No. 3. About 500 cubic centimeters (cc) of the mud was placed in the housing 100 with the outlet 108 in a closed state. In the test illustrated by FIG. 6C, a pressure of 100 psi was applied through the pressure port 110 to simulate the drilling operation with 100 psi overbalance pressure without encountering any loss zones. In the test illustrated by FIG. 6D, the outlet 108 was subsequently opened to simulate encountering a vugular loss zone with a vug size of 10 mm. Visual observation of the test result, enabled by the transparent nature of the housing 102, indicated the loss of only about 100 cc of the bentonite mud through the outlet 108. However, after the initial mud loss, there was no further loss of drilling mud under the action of 100 psi overbalance pressure reflected in the stabilization of the mud level after a while due to no further drop of mud level in the housing 102. The result indicates that the LCM in the mud has crowded and jammed the outlet 108 due to the interweaved and inter-locked fiber mass in the LCM. The result further demonstrates that the apparatus 100 is suitable to evaluate the effectiveness of LCM products and slurries for controlling loss of circulation in vugular loss zones.

Figure 7:
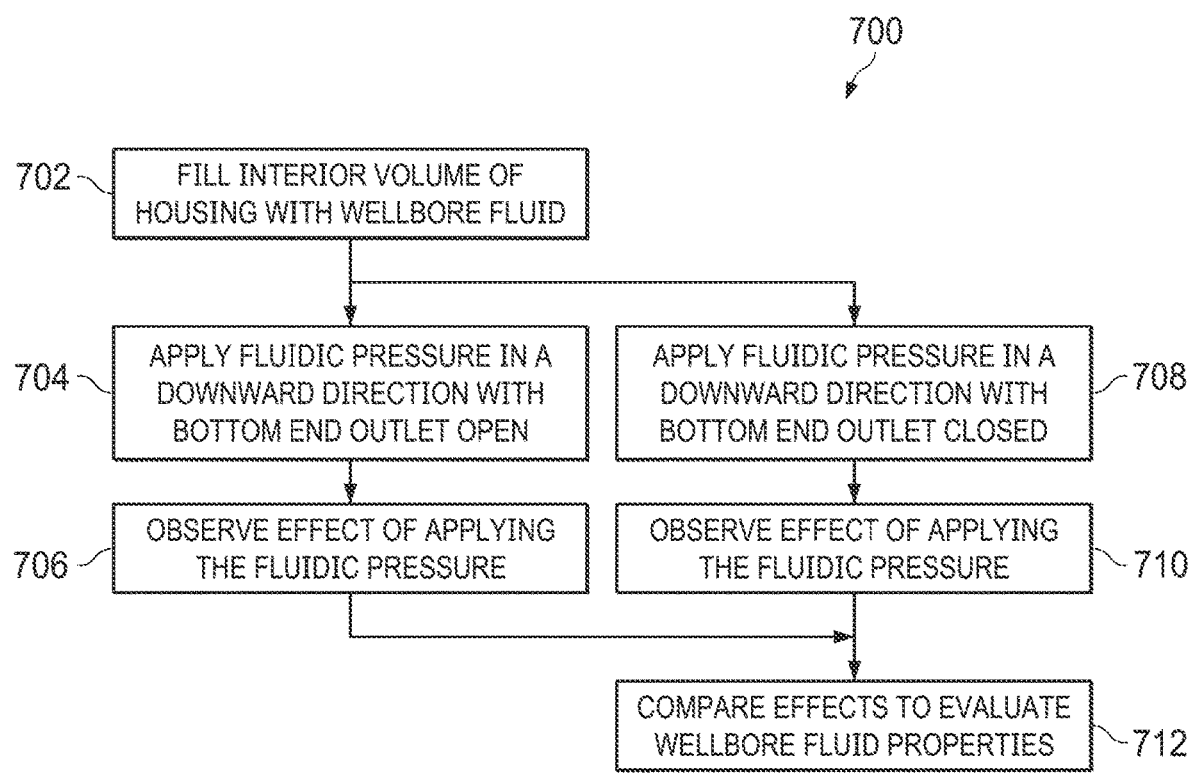
FIG. 7 is a flowchart of an example of a process of performing flow simulation tests using the apparatus of FIG. 1.

FIG. 7 is a flowchart of an example of a process 700 of performing flow simulation tests using the apparatus of FIG. 1. At 702, the inner volume of the housing is filled with wellbore fluid (for example, drilling mud, fracturing fluid, production fluid, or a combination of any fluids that can be flowed through wellbores). At 704, fluidic pressure is applied in a downward direction with bottom end outlet in an open state. At 706, an effect of applying the fluidic pressure is observed. At 708, fluidic pressure applied in the downward direction with bottom end outlet in a closed state. At 710, an effect of applying the fluidic pressure is observed. These steps are repeated for different types of fluids or for the same fluid to which additives are added. At 712, the effects of the observations are compared based on which properties of the wellbore fluid can be evaluated.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results

The invention claimed is:

1. A laboratory test apparatus comprising:
   a mounting stand comprising a horizontal member;
   a housing comprising an upper end attached to the horizontal member of the mounting stand, the housing extending downward from the mounting stand and terminating at a lower end below the mounting stand, the housing defining an inner volume representing an annulus formed by an inner wall of a wellbore being drilled in a hydrocarbon-carrying formation and an outer wall of a drill string used to drill the wellbore, the housing comprising wellbore fluid filling the inner volume;
   a coupling section defined by the mounting stand, wherein the coupling section extends on either side of the horizontal member, wherein the upper end of the housing is coupled to the coupling section;
   a lower cover plate configured to sealingly cover the lower end, the lower cover plate representing the inner wall of the wellbore, the lower cover plate defining an outlet configured to be switched between an open state and a closed state, the outlet in the open state representing a vug in the inner wall of the wellbore; and
   a pressure port defined near the upper end of the housing, the pressure port configured to transmit fluidic pressure in a downward direction from the upper end towards the lower end through the wellbore fluid and to apply the fluidic pressure to the wellbore fluid within the inner volume.

2. The apparatus of claim 1, further comprising a wired screen comprising a mesh having a mesh size and defining an opening, the size and shape of the opening being same as that of the outlet, the wired screen positioned at the lower end, the wired screen cooperating with the lower cover plate to sealingly cover the lower end.

3. The apparatus of claim 2, wherein the pressure port is formed through a circumferential wall of the housing adjacent the upper cover plate.

4. The apparatus of claim 2, wherein the pressure port is formed in the upper cover plate adjacent the housing.

5. The apparatus of claim 1, further comprising an upper cover plate configured to sealingly cover the upper end.

6. The apparatus of claim 1, wherein the housing is transparent.

* * * * *